United States Patent [19]
Vrijbloed et al.

[11] Patent Number: 6,015,705
[45] Date of Patent: Jan. 18, 2000

[54] METHOD OF MODIFYING THE DNA OF AN ORGANISM, DNA SEQUENCE, METHOD OF DETECTION AND ISOLATION OF A GENE CAPABLE OF MODIFYING THE DNA OF AN ORGANISM AND ORGANISMS COMPRISING MODIFIED DNA

[75] Inventors: Jan W. Vrijbloed, Zurich, Switzerland; Lubbert Dijkhuizen, Zuidlaren, Netherlands

[73] Assignee: Rijksuniversiteit Groningen, Groningen, Netherlands

[21] Appl. No.: 08/685,466

[22] Filed: Jul. 24, 1996

Related U.S. Application Data

[60] Provisional application No. 60/001,381, Jul. 24, 1995.

[51] Int. Cl.$^7$ ...................................................... C12N 1/21
[52] U.S. Cl. ...................... 435/252.1; 435/440; 435/455; 435/471; 435/252.3
[58] Field of Search ........................... 435/172.1, 6, 243, 435/252.1, 252.3, 440, 455, 471; 536/23.1

[56] References Cited

PUBLICATIONS

L. de Boer, W. Harder, and L. Dijkhuizen, "Phenylalanine and tyrosine metabolism in the facultative methylotroph *Nocardia* sp. 239," 149 Arch. Microbiol. 459–465 (1988).

J. Cairns, J. Overbaugh, and S. Miller, 355 Nature 142–145 (1988).

G.J.W. Euverink, G.I. Hessels, J.W. Vrijbloed, J.R. Coggins, and L. Dijkhuizen, "Purification and characterization of a dual function 3–hydroquinate dehydratase from *Amycolatopsis methanolica*," 138 J. Gen. Microbiology 2449–2457 (1992).

G.J.W. Euverink, D.J. Wolters, and L. Dijkhuizen, "Prephenate dehydratase of the actinomycete *Amycolatopsis methanolica*: purification and characterization of wild–type and deregulated mutant proteins," 308 Biochem. J. 313–320 (1995).

P. Moretti, G. Hintermann, and R. Hutter, "Isolation and characterization of an extrachromosomal element from *Nocardia mediterranei*," 14 Plasmid 126–133 (1985).

J. W. Vrijbloed, J. Madon, and L. Dijkhuizen, "A plasmid from the methylotrophic actinomycete *Amycolatopsis methanolica* capable of site–specific integration," 176 J. Bacteriol. 7087–7090 (1994).

*Primary Examiner*—Nancy Degen
*Assistant Examiner*—Irem Yucel
*Attorney, Agent, or Firm*—Mayer, Brown & Platt

[57] ABSTRACT

Method of modifying DNA by subjecting the DNA to a mutation-inducing treatment. The method includes the steps of bringing the DNA to be mutated and a gene encoding a mutation-inducing non-DNA polymerase protein together in cells, growing the cells in the presence of a stress factor, and selecting the mutant cells which have developed a desirable trait in the presence of the stress factor.

14 Claims, 7 Drawing Sheets

FIGURE 1A

```
        NarI
  1     GGCGCCCAGCACCTTCGGCAGTAGCCCGCTCCCACCAGTCGGGACCGGAATCATGTTGCC

61     CTTCTTGCCCATGGCTACCTCCCAGGTTCTGCGGCTCGGCGGTTTCCGTTGCCATGCCTC

121     AAGATTCGTCTGGTTCCGGCTTCTTGGGGAGATGAGTCCCTGGTGAGTCGTTGGTGATTC

181     GCTCGACTCACCAGGGGCTGACCAGGCACAATGCCCGCAAGGGAGGTGACCGTGGGGGAC
                                                          fM  G  D
              HindIII
241     AGCGGGGCAACCGAGAGCAAGCTTCGCCGTGCTCGCCTTGCCGCCGGGATGACGCAAGGC
         S  G  A  T  E  S  K  L  R  R  A  R  L  A  A  G  M  T  Q  G 301     GAGGTCCGGGCCAAGCTCACGCAGGCTCGCCGTCGCCGGGGCAAGATGCCCCCGAAGGAA
         E  V  R  A  K  L  T  Q  A  R  R  R  R  G  K  M  P  P  K  E 361     GCCAGCTTGAAGCGGATGTACACGTCGTGGGAGACCGGCGCGGTGATCCCGACGGACTGG
         A  S  L  K  R  M  Y  T  S  W  E  T  G  A  V  I  P  T  D  W 421     CGGGACGAACTGTGCGAGGTATTCGAGCTTCCACCGGCCGCGCTCGGGTTGGTCGAGACC
         R  D  E  L  C  E  V  F  E  L  P  P  A  A  L  G  L  V  E  T 481     ACACCGCCACCTGCGCTCGACCTCCCGAGCACATTCGAGGTGGTCCGGCTCGATCCAGCG
         T  P  P  A  L  D  L  P  S  T  F  E  V  V  R  L  D  P  A
                                                            PstI
541     GTGATTTCGCTGCTAGACCAGCAGACGAACTTCTACCGGCTGCAGGACCGGCTGCTGGGG
         V  I  S  L  L  D  Q  Q  T  N  F  Y  R  L  Q  D  R  L  L  G 601     GCGGCGATCATTCCGCAGACCGAAGCCCACGTCCGCAACCTTGAGCAGATGCTGCGAAAT
         A  A  I  I  P  Q  T  E  A  H  V  R  N  L  E  Q  M  L  R  N 661     GCGCTGCCGAGCGGCCACCTTCCGACAGCGGCGGTGACCCTCGCTGAGGCGGCTGCGCTC
         A  L  P  S  G  H  L  P  T  A  A  V  T  L  A  E  A  A  A  L 721     GCCGGTTGGCAAGCGCTCGATGCGGGTGATCTCCGGAAAGCGTGGGACCTGCACGACATC
         A  G  W  Q  A  L  D  A  G  D  L  R  K  A  W  D  L  H  D  I 781     GCGAAGTCCGCAGCACGGCAGGGGGAGAACCCAGCCGTGCTCGCGCACGTCACGGCGCAG
         A  K  S  A  A  R  Q  G  E  N  P  A  V  L  A  H  V  T  A  Q 841     CAGGCTTACGTTCTGCTCGATGCCGGCCGGGCCGCCGATGCGGTGGAGCTGGTCGAGTAT
         Q  A  Y  V  L  L  D  A  G  R  A  A  D  A  V  E  L  V  E  Y 901     GCAAGCGAACCCAGGCTGCTCGGACAGGTCCCCGCACGCCTTCGGTCGTGGTTGGCCGCG
         A  S  E  P  R  L  L  G  Q  V  P  A  R  L  R  S  W  L  A  A 961     GCGCACGCCGAGTTCCTGGCCGCGGCGGGGGACCGATCCGGCGCGATGCGGCGGCTCGAT
         A  H  A  E  F  L  A  A  A  G  D  R  S  G  A  M  R  R  L  D
                         PvuII
```

FIGURE 1B

```
1021 CAAGCGGCCGACGTGCTGCCAGCTGGCGACAACGACCCTGAGTTGCCGTACCTGATGCTG
      Q  A  A  D  V  L  P  A  G  D  N  D  P  E  L  P  Y  L  M  L

1081 AACGGCGCGCACCTCGCCCGGTGGCGGGGCAACTGCTTGGCGCGACTCGGCGAAGACCAG
      N  G  A  H  L  A  R  W  R  G  N  C  L  A  R  L  G  E  D  Q

1141 GCGATCGAGGACCTGACAGCGGCGCTCGATGGGCTCACCACGCTCACCTCACGGCGAGCA
      A  I  E  D  L  T  A  A  L  D  G  L  T  T  L  T  S  R  R  A

1201 GAGGCGGGGCTTCGTGTAGACCTCGCGCTTGCCCTGCGGAAGCGCGGCGACCTGGACGAG
      E  A  G  L  R  V  D  L  A  L  R  K  R  G  D  L  D  E

1261 TCGCGCGTGCAGGCCCGACAAGCCGCCGAGCTGGCCGGCACAACAGGCTCAGCCCGGCAG
      S  R  V  Q  A  R  Q  A  A  E  L  A  G  T  T  G  S  A  R  Q

1321 CGAGCCCGGATCGCGGAGCTACTTGCCGCCTAGCGCGAGAACGTGCAGCAGCCCGATCAG
      R  A  R  I  A  E  L  L  A  A  -
                           -  K  G  G  L  A  L  V  H  L  L  G  I  L

1381 AGCGCCTGAGTTCCCGACCTGGCCTGCTCGGATGAGGTCGGGAACGTCGCGGAAGGGCAT
      A  G  S  N  G  V  Q  G  A  R  I  L  D  P  V  D  R  F  P  M

1441 CCACTGGAAGGTGCCTTCGTTCTGCTCGGTCGGGTCGGCGACTTGCTCGACGCCTCGGAC
      W  Q  F  T  G  E  N  Q  E  T  P  D  A  V  Q  E  V  G  R  V
                                    SphI                    BclI
1501 GACAAAGAGGTGGTTCGGGTTGCGCAGCATGCCCACCGCGGGCTCGAACGTGATCAGCGG
      V  F  L  H  N  P  N  R  L  M  G  V  A  P  E  F  T  I  L  P

1561 CTCGATCGAGCGCGGCCGGTAGCCGGTCTCTTCCTCGATCTCGCGGACGACGGTCTCCTC
      E  I  S  R  P  R  Y  G  T  E  E  E  I  E  R  V  V  T  E  E
                                                BstXI
1621 AGGGGACTCGTCGCCGTCGATGATGCCGCCGGGTACTTCCCAGCTCCAGATGTTTGGTGC
      P  S  E  D  G  D  I  I  G  G  P  V  E  W  S  I  N  P  A

1681 GAACCTGTGTCGCCAAGCCATGAGAACGTGATCCGCAGTGTCGTTGAAGACGATCGCCAT
      F  R  H  R  W  A  M  L  V  H  D  A  T  D  N  F  V  I  A  M

1741 GGCGACGGGCGGAAACCACACGGTGTGATGCTCGAAGCGCTCGCCCGATGGCTGCGAGAT
      A  V  P  P  F  W  V  T  H  H  E  F  R  E  G  S  P  Q  S  I

1801 GTCGGCTAAGCCGACTTTGACCCACTCGGTCTCGTAGACGGGACGCTCGCCGTGGACGAT
      D  A  L  G  V  K  V  W  E  T  E  Y  V  P  R  E  G  H  V  I

1861 CCATCGGTCCTTGTCCATGGGGATAGGGTCTCCCGCTCTAGCGCTGTGTGGGGTCACGCC
      W  R  D  K  D  M  P  I  P  D  G  A  R  A  S  H  P  T  Mf
                            NspHI
1921 GATGAACCTCCCGTGGGTCGTCTCGCATGT  1950
```

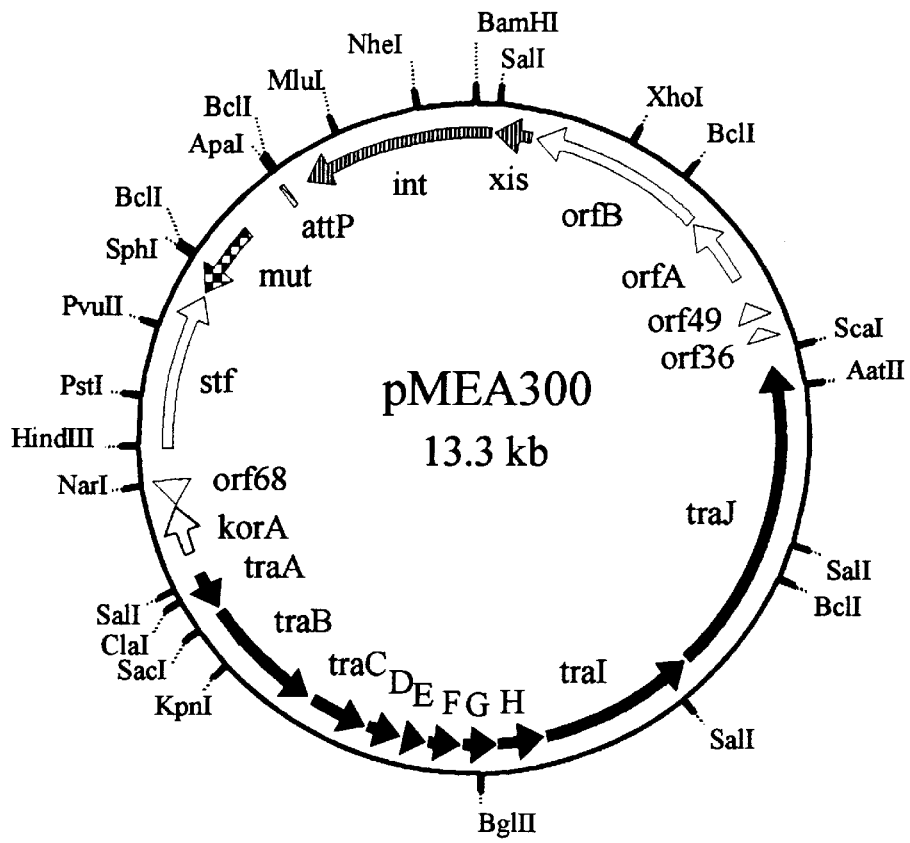
|  | Integration |
|  | Maintenance |
|  | Conjugation, pock formation |
| 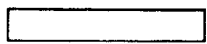 | Stimulation of transformation frequency |
|  | Mutation frequency |
FIGURE 2

FIGURE 4A

The DNA sequence of mut is:

```
  1  GTGACCCCAC ACAGCGCTAG AGCGGGAGAC CCTATCCCCA TGGACAAGGA
 51  CCGATGGATC GTCCACGGCG AGCGTCCCGT CTACGAGACC GAGTGGGTCA
101  AAGTCGGCTT AGCCGACATC TCGCAGCCAT CGGGCGAGCG CTTCGAGCAT
151  CACACCGTGT GGTTTCCGCC CGTCGCCATG GCGATCGTCT TCAACGACAC
201  TGCGGATCAC GTTCTCATGG CTTGGCGACA CAGGTTCGCA CCAAACATCT
251  GGAGCTGGGA AGTACCCGGC GGCATCATCG ACGGCGACGA GTCCCCTGAG
301  GAGACCGTCG TCCGCGAGAT CGAGGAAGAG ACCGGCTACC GGCCGCGCTC
351  GATCGAGCCG CTGATCACGT TCGAGCCCGC GGTGGGCATG CTGCGCAACC
401  CGAACCACCT CTTTGTCGTC CGAGGCGTCG AGCAAGTCGC CGACCCGACC
451  GAGCAGAACG AAGGCACCTT CCAGTGGATG CCCTTCCGCG ACGTTCCCGA
501  CCTCATCCGA GCAGGCCAGG TCGGGAACTC AGGCGCTCTG ATCGGGCTGC
551  TGCACGTTCT CGCGCTAGGC GGCAAGTAG
```

The protein sequence of MUT is:

MetThrProHisSerAlaArgAlaGlyAspProIleProMETAspLysAspArgTrpIleValHisGlyGluArg
ProValTyrGluThrGluTrpValLysValGlyLeuAlaAspIleSerGlnProSerGlyGluArgPheGluHis
HisThrValTrpPheProProValAlaMETAlaIleValPheAsnAspThrAlaAspHisValLeuMETAlaTrp
ArgHisArgPheAlaProAsnIleTrpSerTrpGluValProGlyGlyIleIleAspGlyAspGluSerProGlu
GluThrValValArgGluIleGluGluGluThrGlyTyrArgProArgSerIleGluProLeuIleThrPheGlu
ProAlaValGlyMETLeuArgAsnProAsnHisLeuPheValValArgGlyValGluGlnValAlaAspProThr
GluGlnAsnGluGlyThrPheGlnTrpMETProPheArgAspValProAspLeuIleArgAlaGlyGlnValGly
AsnSerGlyAlaLeuIleGlyLeuLeuHisValLeuAlaLeuGlyGlyLysSTP

The DNA sequence of stf is:

```
  1  GTGGGGGACA GCGGGGCAAC CGAGAGCAAG CTTCGCCGTG CTCGCCTTGC
 51  CGCCGGGATG ACGCAAGGCG AGGTCCGGGC CAAGCTCACG CAGGCTCGCC
101  GTCGCCGGGG CAAGATGCCC CCGAAGGAAG CCAGCTTGAA GCGGATGTAC
151  ACGTCGTGGG AGACCGGCGC GGTGATCCCG ACGGACTGGC GGGACGAACT
```

FIGURE 4B

```
 201  GTGCGAGGTA TTCGAGCTTC CACCGGCCGC GCTCGGGTTG GTCGAGACCA
 251  CACCGCCACC TGCGCTCGAC CTCCCGAGCA CATTCGAGGT GGTCCGGCTC
 301  GATCCAGCGG TGATTTCGCT GCTAGACCAG CAGACGAACT TCTACCGGCT
 351  GCAGGACCGG CTGCTGGGGG CGGCGATCAT TCCGCAGACC GAAGCCCACG
 401  TCCGCAACCT TGAGCAGATG CTGCGAAATG CGCTGCCGAG CGGCCACCTT
 451  CCGACAGCGG CGGTGACCCT CGCTGAGGCG GCTGCGCTCG CCGGTTGGCA
 501  AGCGCTCGAT GCGGGTGATC TCCGGAAAGC GTGGGACCTG CACGACATCG
 551  CGAAGTCCGC AGCACGGCAG GGGGAGAACC CAGCCGTGCT CGCGCACGTC
 601  ACGGCGCAGC AGGCTTACGT TCTGCTCGAT GCCGGCCGGG CCGCCGATGC
 651  GGTGGAGCTG GTCGAGTATG CAAGCGAACC CAGGCTGCTC GGACAGGTCC
 701  CCGCACGCCT TCGGTCGTGG TTGGCCGCGG CGCACGCCGA GTTCCTGGCC
 751  GCGGCGGGGG ACCGATCCGG CGCGATGCGG CGGCTCGATC AAGCGGCCGA
 801  CGTGCTGCCA GCTGGCGACA ACGACCCTGA GTTGCCGTAC CTGATGCTGA
 851  ACGGCGCGCA CCTCGCCCGG TGGCGGGGCA ACTGCTTGGC GCGACTCGGC
 901  GAAGACCAGG CGATCGAGGA CCTGACAGCG GCGCTCGATG GGCTCACCAC
 951  GCTCACCTCA CGGCGAGCAG AGGCGGGGCT TCGTGTAGAC CTCGCGCTTG
1001  CCCTGCGGAA GCGCGGCGAC CTGGACGAGT CGCGCGTGCA GGCCCGACAA
1051  GCCGCCGAGC TGGCCGGCAC AACAGGCTCA GCCCGGCAGC GAGCCCGGAT
1101  CGCGGAGCTA CTTGCCGCCT AG
```

The protein sequence of STF is:

METGlyAspSerGlyAlaThrGluSerLysLeuArgArgAlaArgLeuAlaAlaGlyMETThrGlnGlyGluVal
ArgAlaLysLeuThrGlnAlaArgArgArgArgGlyLysMETProProLysGluAlaSerLeuLysArgMETTyr
ThrSerTrpGluThrGlyAlaValIleProThrAspTrpArgAspGluLeuCysGluValPheGluLeuProPro
AlaAlaLeuGlyLeuValGluThrThrProProAlaLeuAspLeuProSerThrPheGluValValArgLeu
AspProAlaValIleSerLeuLeuAspGlnGlnThrAsnPheTyrArgLeuGlnAspArgLeuLeuGlyAlaAla
IleIleProGlnThrGluAlaHisValArgAsnLeuGluGlnMETLeuArgAsnAlaLeuProSerGlyHisLeu
ProThrAlaAlaValThrLeuAlaGluAlaAlaAlaLeuAlaGlyTrpGlnAlaLeuAspAlaGlyAspLeuArg
LysAlaTrpAspLeuHisAspIleAlaLysSerAlaAlaArgGlnGlyGluAsnProAlaValLeuAlaHisVal
ThrAlaGlnGlnAlaTyrValLeuLeuAspAlaGlyArgAlaAlaAspAlaValGluLeuValGluTyrAlaSer
GluProArgLeuLeuGlyGlnValProAlaArgLeuArgSerTrpLeuAlaAlaAlaHisAlaGluPheLeuAla

FIGURE 4C

AlaAlaGlyAspArgSerGlyAlaMETArgArgLeuAspGlnAlaAlaAspValLeuProAlaGlyAspAsnAsp
ProGluLeuProTyrLeuMETLeuAsnGlyAlaHisLeuAlaArgTrpArgGlyAsnCysLeuAlaArgLeuGly
GluAspGlnAlaIleGluAspLeuThrAlaAlaLeuAspGlyLeuThrThrLeuThrSerArgArgAlaGluAla
GlyLeuArgValAspLeuAlaLeuAlaLeuArgLysArgGlyAspLeuAspGluSerArgValGlnAlaArgGln
AlaAlaGluLeuAlaGlyThrThrGlySerAlaArgGlnArgAlaArgIleAlaGluLeuLeuAlaAlaSTP

SEQUENCE LISTING (1) GENERAL INFORMATION:

(iii) NUMBER OF SEQUENCES: 4

(2) INFORMATION FOR SEQ ID NO:1:

(i) SEQUENCE CHARACTERISTICS:
      (A) LENGTH: 1950 base pairs
      (B) TYPE: nucleic acid
      (C) STRANDEDNESS: single stranded
      (D) TOPOLOGY: linear (x) PUBLICATION INFORMATION:
      (A) AUTHORS: L. de Boer, W. Harder, L. Dijkhuizen
      (B) TITLE: Phenylalanine and tyrosine metabolism in the
          facultative methylotroph Nocardia sp. 239
      (C) JOURNAL: Arch. Microbiol.
      (D) VOLUME: 149
      (F) PAGES: 459-465
      (G) DATE: 1988

(x) PUBLICATION INFORMATION:
      (A) AUTHORS: J. Cairns, J. Overbaugh, S. Miller
      (B) TITLE:
      (C) JOURNAL: Nature
      (D) VOLUME: 335
      (F) PAGES: 142-145
      (G) DATE: 1988

(x) PUBLICATION INFORMATION:
      (A) AUTHORS: G.J.W. Euverink, G.I. Hessels, J.W.
          Vrijbloed, J.R. Coggins, L. Dijkhuizen
      (B) TITLE: Purification and characterization of a dual
          function 3-hydroquinate dehydratase from Amycolatopsis
          methanolica
      (C) JOURNAL: J. Gen. Microbiology
      (D) VOLUME: 138
      (F) PAGES: 2449-2457
      (G) DATE: 1992

(x) PUBLICATION INFORMATION:
      (A) AUTHORS: G.J.W. Euverink, D.J. Wolters, L.
          Dijkhuizen
      (B) TITLE: Prephenate dehydratase of the actinomycete
          Amycolatopsis methanolica: purification and
          characterization of the wild-type and deregulated mutant
          enzymes
      (C) JOURNAL: Biochem. J.
      (D) VOLUME: 308
      (F) PAGES: 313-320
      (G) DATE: 1995

(x) PUBLICATION INFORMATION:
      (A) AUTHORS: P. Moretti, G. Hintermann, R. H tter
      (B) TITLE: Isolation and characterization of an
          extrachromosomal element from Nocardia mediterranei
      (C) JOURNAL: Plasmid
      (D) VOLUME: 14
      (F) PAGES: 126-133
      (G) DATE: 1985

(x) PUBLICATION INFORMATION:
      (A) AUTHORS: J. Sambrook, E.F. Frisch, T. Maniatis
      (B) TITLE: Molecular cloning: a laboratory manual
      (C) JOURNAL: Cold Spring Harbor Laboratory Press
      (G) DATE: 1989

(x) PUBLICATION INFORMATION:
      (A) AUTHORS: J.W. Vrijbloed, J. Madon, L. Dijkhuizen
      (B) TITLE: A plasmid from the methylotrophic
          actinomycete Amycolatopsis methanolica capable of site-specific integration
(C) JOURNAL: J. Bacteriol.
(D) VOLUME: 176
(F) PAGES: 7087-7090
(G) DATE: 1994

(xi) SEQUENCE DESCRIPTION: SEQ ID NO: 1:

```
GGCGCCCAGC ACCTTCGGCA GTAGCCCGCT CCCACCAGTC GGGACCGGAA TCATGTTGCC      60

CTTCTTGCCC ATGGCTACCT CCCAGGTTCT GCGGCTCGGC GGTTTCCGTT GCCATGCCTC     120

AAGATTCGTC TGGTTCCGGC TTCTTGGGGA GATGAGTCCC TGGTGAGTCG TTGGTGATTC     180

GCTCGACTCA CCAGGGGCTG ACCAGGCACA ATGCCCGCAA GGGAGGTGAC C GTG GGG GAC  240
                                                        Met Gly Asp
                                                         1

AGC GGG GCA ACC GAG AGC AAG CTT CGC CGT GCT CGC CTT GCC GCC GGG       288
Ser Gly Ala Thr Glu Ser Lys Leu Arg Arg Ala Arg Leu Ala Ala Gly
     5                  10                  15

ATG ACG CAA GGC GAG GTC CGG GCC AAG CTC ACG CAG GCT CGC CGT CGC       336
Met Thr Gln Gly Glu Val Arg Ala Lys Leu Thr Gln Ala Arg Arg Arg
 20                  25                  30                  35

CGG GGC AAG ATG CCC CCG AAG GAA GCC AGC TTG AAG CGG ATG TAC ACG       384
Arg Gly Lys Met Pro Pro Lys Glu Ala Ser Leu Lys Arg Met Tyr Thr
                 40                  45                  50

TCG TGG GAG ACC GGC GCG GTG ATC CCG ACG GAC TGG CGG GAC GAA CTG       432
Ser Trp Glu Thr Gly Ala Val Ile Pro Thr Asp Trp Arg Asp Glu Leu
             55                  60                  65

TGC GAG GTA TTC GAG CTT CCA CCG GCC GCG CTC GGG TTG GTC GAG ACC       480
Cys Glu Val Phe Glu Leu Pro Pro Ala Ala Leu Gly Leu Val Glu Thr
         70                  75                  80

ACA CCG CCA CCT GCG CTC GAC CTC CCG AGC ACA TTC GAG GTG GTC CGG       528
Thr Pro Pro Pro Ala Leu Asp Leu Pro Ser Thr Phe Glu Val Val Arg
     85                  90                  95

CTC GAT CCA GCG GTG ATT TCG CTG CTA GAC CAG CAG ACG AAC TTC TAC       576
Leu Asp Pro Ala Val Ile Ser Leu Leu Asp Gln Gln Thr Asn Phe Tyr
100                 105                 110                 115

CGG CTG CAG GAC CGG CTG CTG GGG GCG GCG ATC ATT CCG CAG ACC GAA       624
Arg Leu Gln Asp Arg Leu Leu Gly Ala Ala Ile Ile Pro Gln Thr Glu
                120                 125                 130

GCC CAC GTC CGC AAC CTT GAG CAG ATG CTG CGA AAT GCG CTG CCG AGC       672
Ala His Val Arg Asn Leu Glu Gln Met Leu Arg Asn Ala Leu Pro Ser
            135                 140                 145

GGC CAC CTT CCG ACA GCG GCG GTG ACC CTC GCT GAG GCG GCT GCG CTC       720
Gly His Leu Pro Thr Ala Ala Val Thr Leu Ala Glu Ala Ala Ala Leu
        150                 155                 160

GCC GGT TGG CAA GCG CTC GAT GCG GGT GAT CTC CGG AAA GCG TGG GAC       768
Ala Gly Trp Gln Ala Leu Asp Ala Gly Asp Leu Arg Lys Ala Trp Asp
    165                 170                 175

CTG CAC GAC ATC GCG AAG TCC GCA GCA CGG CAG GGG GAG AAC CCA GCC       816
Leu His Asp Ile Ala Lys Ser Ala Ala Arg Gln Gly Glu Asn Pro Ala
180                 185                 190                 195

GTG CTC GCG CAC GTC ACG GCG CAG CAG GCT TAC GTT CTG CTC GAT GCC       864
Val Leu Ala His Val Thr Ala Gln Gln Ala Tyr Val Leu Leu Asp Ala
                200                 205                 210

GGC CGG GCC GCC GAT GCG GTG GAG CTG GTC GAG TAT GCA AGC GAA CCC       912
Gly Arg Ala Ala Asp Ala Val Glu Leu Val Glu Tyr Ala Ser Glu Pro
            215                 220                 225

AGG CTG CTC GGA CAG GTC CCC GCA CGC CTT CGG TCG TGG TTG GCC GCG       960
Arg Leu Leu Gly Gln Val Pro Ala Arg Leu Arg Ser Trp Leu Ala Ala
        230                 235                 240

GCG CAC GCC GAG TTC CTG GCC GCG GCG GGG GAC CGA TCC GGC GCG ATG      1008
Ala His Ala Glu Phe Leu Ala Ala Ala Gly Asp Arg Ser Gly Ala Met
```

-continued

```
              245                 250                 255
CGG CGG CTC GAT CAA GCG GCC GAC GTG CTG CCA GCT GGC GAC AAC GAC     1056
Arg Arg Leu Asp Gln Ala Ala Asp Val Leu Pro Ala Gly Asp Asn Asp
260                 265                 270                 275

CCT GAG TTG CCG TAC CTG ATG CTG AAC GGC GCG CAC CTC GCC CGG TGG     1104
Pro Glu Leu Pro Tyr Leu Met Leu Asn Gly Ala His Leu Ala Arg Trp
                280                 285                 290

CGG GGC AAC TGC TTG GCG CGA CTC GGC GAA GAC CAG GCG ATC GAG GAC     1152
Arg Gly Asn Cys Leu Ala Arg Leu Gly Glu Asp Gln Ala Ile Glu Asp
            295                 300                 305

CTG ACA GCG GCG CTC GAT GGG CTC ACC ACG CTC ACC TCA CGG CGA GCA     1200
Leu Thr Ala Ala Leu Asp Gly Leu Thr Thr Leu Thr Ser Arg Arg Ala
        310                 315                 320

GAG GCG GGG CTT CGT GTA GAC CTC GCG CTT GCC CTG CGG AAG CGC GGC     1248
Glu Ala Gly Leu Arg Val Asp Leu Ala Leu Ala Leu Arg Lys Arg Gly
    325                 330                 335

GAC CTG GAC GAG TCG CGC GTG CAG GCC CGA CAA GCC GCC GAG CTG GCC     1296
Asp Leu Asp Glu Ser Arg Val Gln Ala Arg Gln Ala Ala Glu Leu Ala
340                 345                 350                 355

GGC ACA ACA GGC TCA GCC CGG CAG CGA GCC CGG ATC GCG GAG CTA CTT     1344
Gly Thr Thr Gly Ser Ala Arg Gln Arg Ala Arg Ile Ala Glu Leu Leu
                360                 365                 370

GCC GCC TAG CGCGAGAACG TGCAGCAGCC CGATCAGAGC GCCTGAGTTC CCGACCTGGC  1403
Ala Ala

CTGCTCGGAT GAGGTCGGGA ACGTCGCGGA AGGGCATCCA CTGGAAGGTG CCTTCGTTCT    1463

GCTCGGTCGG GTCGGCGACT TGCTCGACGC CTCGGACGAC AAAGAGGTGG TTCGGGTTGC    1523

GCAGCATGCC CACCGCGGGC TCGAACGTGA TCAGCGGCTC GATCGAGCGC GGCCGGTAGC    1583

CGGTCTCTTC CTCGATCTCG CGGACGACGG TCTCCTCAGG GGACTCGTCG CCGTCGATGA    1643

TGCCGCCGGG TACTTCCCAG CTCCAGATGT TGGTGCGAA CCTGTGTCGC CAAGCCATGA     1703

GAACGTGATC CGCAGTGTCG TTGAAGACGA TCGCCATGGC GACGGGCGGA AACCACACGG    1763

TGTGATGCTC GAAGCGCTCG CCCGATGGCT GCGAGATGTC GGCTAAGCCG ACTTTGACCC    1823

ACTCGGTCTC GTAGACGGGA CGCTCGCCGT GGACGATCCA TCGGTCCTTG TCCATGGGGA    1883

TAGGGTCTCC CGCTCTAGCG CTGTGTGGGG TCACGCCGAT GAACCTCCCG TGGGTCGTCT    1943

CGCATGT                                                              1950
```

(2) INFORMATION FOR SEQ ID NO:2:

(i) SEQUENCE CHARACTERISTICS:
        (A) LENGTH: 373 amino acids
        (B) TYPE: amino acid
        (D) TOPOLOGY: linear (ix) FEATURE:
        (A) NAME/KEY: Modified amino acid, formylmethionine
        (B) LOCATION: The first amino acid in the sequence,
            described as methionine, is actually known as
            formylmethionine ("fMet"). Polypeptide chains in
            bacteria often start with formylmethionine.

(x) PUBLICATION INFORMATION:
        (A) AUTHORS: L. de Boer, W. Harder, L. Dijkhuizen
        (B) TITLE: Phenylalanine and tyrosine metabolism in the
            facultative methylotroph Nocardia sp. 239
        (C) JOURNAL: Arch. Microbiol.
        (D) VOLUME: 149
        (F) PAGES: 459-465
        (G) DATE: 1988

(x) PUBLICATION INFORMATION:
        (A) AUTHORS: J. Cairns, J. Overbaugh, S. Miller
        (B) TITLE:

-continued

```
            (C) JOURNAL: Nature
            (D) VOLUME: 335
            (F) PAGES: 142-145
            (G) DATE: 1988

(x) PUBLICATION INFORMATION:
            (A) AUTHORS: G.J.W. Euverink, G.I. Hessels, J.W.
                Vrijbloed, J.R. Coggins, L. Dijkhuizen
            (B) TITLE: Purification and characterization of a dual
                function 3-hydroquinate dehydratase from Amycolatopsis
                methanolica
            (C) JOURNAL: J. Gen. Microbiology
            (D) VOLUME: 138
            (F) PAGES: 2449-2457
            (G) DATE: 1992

(x) PUBLICATION INFORMATION:
            (A) AUTHORS: G.J.W. Euverink, D.J. Wolters, L.
                Dijkhuizen
            (B) TITLE: Prephenate dehydratase of the actinomycete
                Amycolatopsis methanolica: purification and
                characterization of the wild-type and deregulated mutant
                enzymes
            (C) JOURNAL: Biochem. J.
            (D) VOLUME: 308
            (F) PAGES: 313-320
            (G) DATE: 1995

(x) PUBLICATION INFORMATION:
            (A) AUTHORS: P. Moretti, G. Hintermann, R. H tter
            (B) TITLE: Isolation and characterization of an
                extrachromosomal element from Nocardia mediterranei
            (C) JOURNAL: Plasmid
            (D) VOLUME: 14
            (F) PAGES: 126-133
            (G) DATE: 1985

(x) PUBLICATION INFORMATION:
            (A) AUTHORS: J. Sambrook, E.F. Frisch, T. Maniatis
            (B) TITLE: Molecular cloning: a laboratory manual
            (C) JOURNAL: Cold Spring Harbor Laboratory Press
            (G) DATE: 1989

(x) PUBLICATION INFORMATION:
            (A) AUTHORS: J.W. Vrijbloed, J. Madon, L. Dijkhuizen
            (B) TITLE: A plasmid from the methylotrophic
                actinomycete Amycolatopsis methanolica capable of site-
                specific integration
            (C) JOURNAL: J. Bacteriol.
            (D) VOLUME: 176
            (F) PAGES: 7087-7090
            (G) DATE: 1994

(xi) SEQUENCE DESCRIPTION: SEQ ID NO: 2:

Met Gly Asp Ser Gly Ala Thr Glu Ser Lys Leu Arg Arg Ala Arg Leu
1               5                   10                  15

Ala Ala Gly Met Thr Gln Gly Glu Val Arg Ala Lys Leu Thr Gln Ala
                20                  25                  30

Arg Arg Arg Arg Gly Lys Met Pro Pro Lys Glu Ala Ser Leu Lys Arg
            35                  40                  45

Met Tyr Thr Ser Trp Glu Thr Gly Ala Val Ile Pro Thr Asp Trp Arg
    50                  55                  60

Asp Glu Leu Cys Glu Val Phe Glu Leu Pro Ala Ala Leu Gly Leu
65                  70                  75                  80

Val Glu Thr Thr Pro Pro Pro Ala Leu Asp Leu Pro Ser Thr Phe Glu
                85                  90                  95

Val Val Arg Leu Asp Pro Ala Val Ile Ser Leu Leu Asp Gln Gln Thr
                100                 105                 110

Asn Phe Tyr Arg Leu Gln Asp Arg Leu Leu Gly Ala Ala Ile Ile Pro
            115                 120                 125

Gln Thr Glu Ala His Val Arg Asn Leu Glu Gln Met Leu Arg Asn Ala
```

```
                      130                 135                 140
Leu Pro Ser Gly His Leu Pro Thr Ala Ala Val Thr Leu Ala Glu Ala
145                 150                 155                 160

Ala Ala Leu Ala Gly Trp Gln Ala Leu Asp Ala Gly Asp Leu Arg Lys
                165                 170                 175

Ala Trp Asp Leu His Asp Ile Ala Lys Ser Ala Ala Arg Gln Gly Glu
                180                 185                 190

Asn Pro Ala Val Leu Ala His Val Thr Ala Gln Gln Ala Tyr Val Leu
                195                 200                 205

Leu Asp Ala Gly Arg Ala Ala Asp Ala Val Glu Leu Val Glu Tyr Ala
                210                 215                 220

Ser Glu Pro Arg Leu Leu Gly Gln Val Pro Ala Arg Leu Arg Ser Trp
225                 230                 235                 240

Leu Ala Ala His Ala Glu Phe Leu Ala Ala Gly Asp Arg Ser
                245                 250                 255

Gly Ala Met Arg Arg Leu Asp Gln Ala Ala Asp Val Leu Pro Ala Gly
                260                 265                 270

Asp Asn Asp Pro Glu Leu Pro Tyr Leu Met Leu Asn Gly Ala His Leu
                275                 280                 285

Ala Arg Trp Arg Gly Asn Cys Leu Ala Arg Leu Gly Glu Asp Gln Ala
                290                 295                 300

Ile Glu Asp Leu Thr Ala Ala Leu Asp Gly Leu Thr Thr Leu Thr Ser
305                 310                 315                 320

Arg Arg Ala Glu Ala Gly Leu Arg Val Asp Leu Ala Leu Ala Leu Arg
                325                 330                 335

Lys Arg Gly Asp Leu Asp Glu Ser Arg Val Gln Ala Arg Gln Ala Ala
                340                 345                 350

Glu Leu Ala Gly Thr Thr Gly Ser Ala Arg Gln Arg Ala Arg Ile Ala
                355                 360                 365

Glu Leu Leu Ala Ala
        370

(2) INFORMATION FOR SEQ ID NO:3:

(i) SEQUENCE CHARACTERISTICS:
        (A) LENGTH: 612 base pairs
        (B) TYPE: nucleic acid
        (C) STRANDEDNESS: single stranded
        (D) TOPOLOGY: linear (x) PUBLICATION INFORMATION:
        (A) AUTHORS: L. de Boer, W. Harder, L. Dijkhuizen
        (B) TITLE: Phenylalanine and tyrosine metabolism in the
            facultative methylotroph Nocardia sp. 239
        (C) JOURNAL: Arch. Microbiol.
        (D) VOLUME: 149
        (F) PAGES: 459-465
        (G) DATE: 1988

(x) PUBLICATION INFORMATION:
        (A) AUTHORS: J. Cairns, J. Overbaugh, S. Miller
        (B) TITLE:
        (C) JOURNAL: Nature
        (D) VOLUME: 335
        (F) PAGES: 142-145
        (G) DATE: 1988

(x) PUBLICATION INFORMATION:
        (A) AUTHORS: G.J.W. Euverink, G.I. Hessels, J.W.
            Vrijbloed, J.R. Coggins, L. Dijkhuizen
        (B) TITLE: Purification and characterization of a dual
            function 3-hydroquinate dehydratase from Amycolatopsis
            methanolica
        (C) JOURNAL: J. Gen. Microbiology
```

(D) VOLUME: 138
(F) PAGES: 2449-2457
(G) DATE: 1992

(x) PUBLICATION INFORMATION:
    (A) AUTHORS: G.J.W. Euverink, D.J. Wolters, L. Dijkhuizen
    (B) TITLE: Prephenate dehydratase of the actinomycete Amycolatopsis methanolica: purification and characterization of the wild-type and deregulated mutant enzymes
    (C) JOURNAL: Biochem. J.
    (D) VOLUME: 308
    (F) PAGES: 313-320
    (G) DATE: 1995

(x) PUBLICATION INFORMATION:
    (A) AUTHORS: P. Moretti, G. Hintermann, R. H tter
    (B) TITLE: Isolation and characterization of an extrachromosomal element from Nocardia mediterranei
    (C) JOURNAL: Plasmid
    (D) VOLUME: 14
    (F) PAGES: 126-133
    (G) DATE: 1985

(x) PUBLICATION INFORMATION:
    (A) AUTHORS: J. Sambrook, E.F. Frisch, T. Maniatis
    (B) TITLE: Molecular cloning: a laboratory manual
    (C) JOURNAL: Cold Spring Harbor Laboratory Press
    (G) DATE: 1989

(x) PUBLICATION INFORMATION:
    (A) AUTHORS: J.W. Vrijbloed, J. Madon, L. Dijkhuizen
    (B) TITLE: A plasmid from the methylotrophic actinomycete Amycolatopsis methanolica capable of site-specific integration
    (C) JOURNAL: J. Bacteriol.
    (D) VOLUME: 176
    (F) PAGES: 7087-7090
    (G) DATE: 1994

(xi) SEQUENCE DESCRIPTION: SEQ ID NO: 3:

```
ACATGCGAGA CGACCCACGG GAGGTTCATC GGC GTG ACC CCA CAC AGC GCT AGA      54
                                    Met Thr Pro His Ser Ala Arg
                                     1               5

GCG GGA GAC CCT ATC CCC ATG GAC AAG GAC CGA TGG ATC GTC CAC GGC     102
Ala Gly Asp Pro Ile Pro Met Asp Lys Asp Arg Trp Ile Val His Gly
         10              15                  20

GAG CGT CCC GTC TAC GAG ACC GAG TGG GTC AAA GTC GGC TTA GCC GAC     150
Glu Arg Pro Val Tyr Glu Thr Glu Trp Val Lys Val Gly Leu Ala Asp
     25                  30                  35

ATC TCG CAG CCA TCG GGC GAG CGC TTC GAG CAT CAC ACC GTG TGG TTT     198
Ile Ser Gln Pro Ser Gly Glu Arg Phe Glu His His Thr Val Trp Phe
 40                  45                  50                  55

CCG CCC GTC GCC ATG GCG ATC GTC TTC AAC GAC ACT GCG GAT CAC GTT     246
Pro Pro Val Ala Met Ala Ile Val Phe Asn Asp Thr Ala Asp His Val
                 60                  65                  70

CTC ATG GCT TGG CGA CAC AGG TTC GCA CCA AAC ATC TGG AGC TGG GAA     294
Leu Met Ala Trp Arg His Arg Phe Ala Pro Asn Ile Trp Ser Trp Glu
             75                  80                  85

GTA CCC GGC GGC ATC ATC GAC GGC GAC GAG TCC CCT GAG GAG ACC GTC     342
Val Pro Gly Gly Ile Ile Asp Gly Asp Glu Ser Pro Glu Glu Thr Val
         90                  95                 100

GTC CGC GAG ATC GAG GAA GAG ACC GGC TAC CGG CCG CGC TCG ATC GAG     390
Val Arg Glu Ile Glu Glu Glu Thr Gly Tyr Arg Pro Arg Ser Ile Glu
    105                 110                 115

CCG CTG ATC ACG TTC GAG CCC GCG GTG GGC ATG CTG CGC AAC CCG AAC     438
Pro Leu Ile Thr Phe Glu Pro Ala Val Gly Met Leu Arg Asn Pro Asn
120                 125                 130                 135

CAC CTC TTT GTC GTC CGA GGC GTC GAG CAA GTC GCC GAC CCG ACC GAG     486
```

```
His Leu Phe Val Val Arg Gly Val Glu Gln Val Ala Asp Pro Thr Glu
        140                 145                 150

CAG AAC GAA GGC ACC TTC CAG TGG ATG CCC TTC CGC GAC GTT CCC GAC       534
Gln Asn Glu Gly Thr Phe Gln Trp Met Pro Phe Arg Asp Val Pro Asp
            155                 160                 165

CTC ATC CGA GCA GGC CAG GTC GGG AAC TCA GGC GCT CTG ATC GGG CTG       582
Leu Ile Arg Ala Gly Gln Val Gly Asn Ser Gly Ala Leu Ile Gly Leu
        170                 175                 180

CTG CAC GTT CTC GCG CTA GGC GGC AAG TAG                               612
Leu His Val Leu Ala Leu Gly Gly Lys
    185                 190
```

(2) INFORMATION FOR SEQ ID NO:4:

(i) SEQUENCE CHARACTERISTICS:
        (A) LENGTH: 192 amino acids
        (B) TYPE: amino acid
        (D) TOPOLOGY: linear (ix) FEATURE:
        (A) NAME/KEY: Modified amino acid, formylmethionine
        (B) LOCATION: The first amino acid in the sequence,
            described as methionine, is actually known as
            formylmethionine ("fMet"). Polypeptide chains in
            bacteria often start with formylmethionine.

(x) PUBLICATION INFORMATION:
        (A) AUTHORS: L. de Boer, W. Harder, L. Dijkhuizen
        (B) TITLE: Phenylalanine and tyrosine metabolism in the
            facultative methylotroph Nocardia sp. 239
        (C) JOURNAL: Arch. Microbiol.
        (D) VOLUME: 149
        (F) PAGES: 459-465
        (G) DATE: 1988

(x) PUBLICATION INFORMATION:
        (A) AUTHORS: J. Cairns, J. Overbaugh, S. Miller
        (B) TITLE:
        (C) JOURNAL: Nature
        (D) VOLUME: 335
        (F) PAGES: 142-145
        (G) DATE: 1988

(x) PUBLICATION INFORMATION:
        (A) AUTHORS: G.J.W. Euverink, G.I. Hessels, J.W.
            Vrijbloed, J.R. Coggins, L. Dijkhuizen
        (B) TITLE: Purification and characterization of a dual
            function 3-hydroquinate dehydratase from Amycolatopsis
            methanolica
        (C) JOURNAL: J. Gen. Microbiology
        (D) VOLUME: 138
        (F) PAGES: 2449-2457
        (G) DATE: 1992

(x) PUBLICATION INFORMATION:
        (A) AUTHORS: G.J.W. Euverink, D.J. Wolters, L.
            Dijkhuizen
        (B) TITLE: Prephenate dehydratase of the actinomycete
            Amycolatopsis methanolica: purification and
            characterization of the wild-type and deregulated mutant
            enzymes
        (C) JOURNAL: Biochem. J.
        (D) VOLUME: 308
        (F) PAGES: 313-320
        (G) DATE: 1995

(x) PUBLICATION INFORMATION:
        (A) AUTHORS: P. Moretti, G. Hintermann, R. H tter
        (B) TITLE: Isolation and characterization of an
            extrachromosomal element from Nocardia mediterranei
        (C) JOURNAL: Plasmid
        (D) VOLUME: 14
        (F) PAGES: 126-133
        (G) DATE: 1985

(x) PUBLICATION INFORMATION:

-continued

```
        (A) AUTHORS: J. Sambrook, E.F. Frisch, T. Maniatis
        (B) TITLE: Molecular cloning: a laboratory manual
        (C) JOURNAL: Cold Spring Harbor Laboratory Press
        (G) DATE: 1989

(x) PUBLICATION INFORMATION:
        (A) AUTHORS: J.W. Vrijbloed, J. Madon, L. Dijkhuizen
        (B) TITLE: A plasmid from the methylotrophic
            actinomycete Amycolatopsis methanolica capable of site-
            specific integration
        (C) JOURNAL: J. Bacteriol.
        (D) VOLUME: 176
        (F) PAGES: 7087-7090
        (G) DATE: 1994

(xi) SEQUENCE DESCRIPTION: SEQ ID NO: 4:

Met Thr Pro His Ser Ala Arg Ala Gly Asp Pro Ile Pro Met Asp Lys
1               5                   10                  15

Asp Arg Trp Ile Val His Gly Glu Arg Pro Val Tyr Glu Thr Glu Trp
            20                  25                  30

Val Lys Val Gly Leu Ala Asp Ile Ser Gln Pro Ser Gly Glu Arg Phe
        35                  40                  45

Glu His His Thr Val Trp Phe Pro Pro Val Ala Met Ala Ile Val Phe
    50                  55                  60

Asn Asp Thr Ala Asp His Val Leu Met Ala Trp Arg His Arg Phe Ala
65              70                  75                  80

Pro Asn Ile Trp Ser Trp Glu Val Pro Gly Gly Ile Ile Asp Gly Asp
            85                  90                  95

Glu Ser Pro Glu Glu Thr Val Val Arg Glu Ile Glu Glu Thr Gly
            100                 105                 110

Tyr Arg Pro Arg Ser Ile Glu Pro Leu Ile Thr Phe Glu Pro Ala Val
            115                 120                 125

Gly Met Leu Arg Asn Pro Asn His Leu Phe Val Val Arg Gly Val Glu
    130                 135                 140

Gln Val Ala Asp Pro Thr Glu Gln Asn Glu Gly Thr Phe Gln Trp Met
145                 150                 155                 160

Pro Phe Arg Asp Val Pro Asp Leu Ile Arg Ala Gly Gln Val Gly Asn
            165                 170                 175

Ser Gly Ala Leu Ile Gly Leu Leu His Val Leu Ala Leu Gly Gly Lys
            180                 185                 190
```

METHOD OF MODIFYING THE DNA OF AN ORGANISM, DNA SEQUENCE, METHOD OF DETECTION AND ISOLATION OF A GENE CAPABLE OF MODIFYING THE DNA OF AN ORGANISM AND ORGANISMS COMPRISING MODIFIED DNA

RELATED APPLICATION

This application claims the benefit of U.S. Provisional Application No. 60/001,381, filed Jul. 24, 1995, which is incorporated by reference herein.

FIELD OF THE INVENTION

The present invention relates to a method of modifying the DNA of an organism, in particular of obtaining an organism capable of overproducing amino acids, antibiotics or proteins or able to degrade xenobiotics, wherein the DNA is subjected to a mutation-inducing treatment and a mutant organism with a desired trait is selected.

BACKGROUND OF THE INVENTION

Methods are known whereby an organism is treated with mutagens such as base analogues (for example 5-bromouracil and 2-aminopurine), substances that chemically modify bases (for example hydroxylamine) or intercalating agents (for example acridines).

This known method requires the addition of chemicals which are hazardous for both the technician handling them and, if not properly disposed of, to the environment. In addition, the modifications are not directed. That is, all the DNA of the organism is mutated and thus an organism with the desired trait will be selected carrying also many other mutations, which mutations may decrease its suitability for the intended use.

It is known that defective DNA polymerase results in an increase in mutations and may result in a desired mutated organism, but replication with defective DNA polymerase does not result in directed mutations. Cairns et al. (1988) describe the phenomenon of adaptive or selection-induced mutation, but this reference does not suggest the method of the present invention.

SUMMARY OF THE INVENTION

It is an object of the present invention to provide a method of modifying the DNA, in particular of directed modification (also referred to as adaptive modification) of the DNA of an organism. In addition it is an object to provide an environmentally friendly method obviating the use of hazardous mutagens.

In accordance a method is provided characterized in that in an organism a gene encoding a mutation-inducing, non-DNA polymerase protein is brought together with the DNA to be mutated, and the organism is grown in the presence of a stress factor while the gene is expressed.

The applicants have found that genes exist which, upon expression, allow the introduction of mutations, in particular, in a way that suggests that the mutations are directed mutations. That is, in the presence of a stress factor those mutations appear to be favored which relieve the stress for the organism. Thus, for example, if an antibiotic is added as the stress factor, those mutations which allow the organism to grow in the presence of the antibiotic are favored.

According to a preferred embodiment the DNA to be mutated and the gene encoding a mutation-inducing protein are separated after the induction of mutations.

Thus, in case of accidental release of the mutated organism into the environment, the organism is no longer equipped with the means to rapidly adapt to the more hostile environment. This decreases its chances of survival, which increases the safety of the method for the environment.

The invention also relates to a method of improving the genetic stability of an organism comprising a gene encoding a mutation-inducing non-DNA polymerase protein, wherein said gene is disabled by methods known per se.

BRIEF DESCRIPTION OF THE DRAWINGS

FIG. 1 is a DNA sequence of the present invention encoding a mutation inducing non-DNA polymerase protein, which protein is encoded from the complementary strand of the DNA sequence from nucleotide 1878 to 1339. Besides the nucleic acid sequence and amino acid sequence of the mut gene, FIG. 1 contains the nucleic acid sequence of a gene stimulating the transformation frequency, as well as its putative amino acid sequence.

FIG. 2 is a restriction map of plasmid pMEA300.

FIG. 4 shows the DNA and amino acid sequences of the mut and stf genes of the present invention.

DETAILED DESCRIPTION OF THE INVENTION

Figure 3:
FIG. 3 shows the spontaneous resistance of wild-type, a pMEA300-free strain (WV1) and strain WV1 carrying pMEA300 against 1 mg/ml para-fluoro phenylalanine.

The following terms are used throughout this description with the meanings defined below.

The term vector means a plasmid, phage or other such DNA molecule, as is well-known in the art, which may or may not be capable of being integrated in the chromosome of a host organism, and which is capable of being maintained in the host organism.

The term organism comprises any organism, prokaryotic or eucaryotic, single cell or multicellular, animal or vegetable, capable of maintaining and expressing said vector.

The term directed or adaptive mutation means the specific mutation of DNA relating to the stress factor.

The term stress factor refers to any chemical or physical factor, such as growth-inhibiting compounds and extreme temperature, as well as the absence of a suitable or essential substrate, which causes an organism to grow less well than without the stress factor.

The term xenobiotic refers to any compound which is not a compound naturally encountered by the organism, and which compound is desired to be degraded into compounds considered less harmful or harmless to man or the environment, or to be converted into a useful compound.

The term disabled in "gene is disabled" relates to a method as a result of which either the gene is no longer expressed, or, in the case the gene is expressed, the resulting protein product is not functionally active as a mutation-inducing non-DNA polymerase protein. As is known in the art, a gene can be disabled in many ways, for example by deleting it completely or partially, or by substituting at least one nucleotide by at least one other nucleotide or nucleotide sequence.

For many biotechnology applications, it is desired to have organisms with more desirable traits. For example, it is desirable to have organisms capable of degrading toxic substances. Even if such an organism is available, it may not be effective under all conceivable circumstances. For example, in land farming relatively low temperatures or the presence of heavy metals or other toxic compounds may render the organism ineffective.

Other biotechnology applications involve the production of antibiotics, (recombinant) proteins and amino acids. It is often desirable to increase the production of these products. The present invention is applicable to these and other areas, as will be evident to one of ordinary skill in the art, allowing production of desirable compounds in higher yields as well as allowing the development of organisms capable of degrading xenobiotics even under unfavorable conditions.

The actinomycete *Amycolatopsis methanolica* contains a 13.3 kb plasmid pMEA300 (Vrijbloed et al., 1994). FIG. 2 details the restriction map of pMEA300. This plasmid is capable of site-specific integration into the genome of the organism. As a result of the investigation of *A. methanolica*, it was surprisingly found that a gene which is carried by this plasmid is capable of introducing adaptive mutations into the DNA of an organism while it is under stress. This gene is referred to as the mut gene. Under conditions of stress, the mutation frequency increases over 100-fold in cells that contain pMEA300.

It is expected that other such genes exist in other organisms, such as the closely related *Amycolatopsis mediterranei* (genus Nocardia) and *Saccharopolyspora erythraea*, as well as in more distantly related and unrelated organisms. Such genes may be found by using assays for activity, or hybridization techniques using part of the DNA sequence of the gene identified within pMEA300 as a probe, or a complementary strand thereof, because of the genetic resemblance with the gene of pMEA300. Alternatively, pMEA300 derivatives may be used.

Therefore, a method is provided which allows for the directed mutation of DNA using said mutation-introducing genes. The invention eliminates the use of hazardous mutagenic compounds, though it is recognized that xenobiotic compounds, which are to be broken down and are added as stress factors, may be mutagenic themselves. This elimination of mutagenic compounds increases the safety of the technician and obviates the disposal of the toxic waste resulting from an experiment with mutagenic compounds.

It is hypothesized that a stress factor results in an increased level of the mutation-inducing non-DNA polymerase protein. The DNA present in the organism is mutated randomly. If a mutation occurs that relieves the stress due to the stress factor, the expression of the mutation-inducing non-DNA polymerase protein is reduced to its ordinary level. Thus, in contrast to chemical mutagenesis or mutations due to a defective DNA polymerase, the DNA of the organism is not mutated more than necessary, i.e., after the desired mutation has been brought about. Consequently, the average number of mutations per organism for every desired mutant is lower, hence directed mutation.

From the above it will be clear that the method according to the invention is very versatile. A deliberate choice of stress factor will result in an organism with the desired trait. For example, adding a stress factor inhibiting the synthesis of a certain amino acid will result in a mutated organism capable of expressing the amino acid in sufficient quantities in the presence of the stress factor. If the stress factor is removed the organism may well overproduce the amino acid. In a similar way it is possible to increase the yield of proteins, antibiotics and other such compounds produced in the organism.

For example, if an organism is not or only barely capable of growing on a certain carbon source and that is the only carbon source available, mutant organisms may be selected for their increased ability to grow on that particular carbon source. The method according to the invention greatly increases the naturally occurring (i.e. spontaneous) mutation frequency.

The method according to the invention may also be used to obtain an organism capable of overproducing recombinant proteins. When an organism is induced to produce a recombinant protein, its resources are partly used to accomplish this task. If a gene encoding a mutation-inducing protein is introduced and expressed in the organism, the organism may end up better capable of dealing with the stress it is under while producing recombinant protein. Although a large proportion of the mutations may involve the elimination of the activity producing the recombinant protein, other mutations may involve beneficial mutations.

The presence of the gene encoding a mutation-inducing protein may offset the benefit of the elimination of the use of mutagens should the mutated organisms be accidentally released into the environment. As it is generally considered undesirable that organisms containing DNA that has been tampered with are released into the environment, the organisms chosen for use are usually incapable of maintaining themselves when released. If they had the ability of rapidly adapting to stress conditions, the released organism could overcome this situation. Therefore it is desirable to separate the gene and the mutated DNA.

According to one embodiment, the gene resides in a vector, the organism carrying the DNA to be mutated is transformed with said vector, a desired mutant organism is selected and cured from said vector. This provides a simple method of obtaining the desired mutant organism.

According to another embodiment the DNA to be mutated resides in a vector, an organism carrying the gene is transformed with said vector, a desired mutant organism is selected and the mutated vector is used to transform a second organism.

Thus, a second organism can be chosen which does not contain any undesired mutated DNA and which is optimal for the particular purpose. The second organism is not necessarily different from the original organism which was used to modify the DNA. On the other hand, the second organism may be entirely different, as long as the vector can be replicated and the gene expressed in the second organism.

The invention also relates to a DNA sequence encoding a mutation-inducing non-DNA polymerase protein, said DNA sequence having the complementary sequence of nucleotides 1917 to 1339 as shown in FIG. 1. FIG. 4 likewise shows the complementary DNA sequence (nucleotides 1 to 579) (SEQ ID NO. 3) and the protein sequence of the invention. In addition, the invention encompasses DNA sequences encoding proteins with activity similar to those encoded by the DNA sequences of FIG. 4.

The DNA sequence shown in FIG. 4 is from the open reading frame 179 (orf179) which region is responsible for the increased mutation frequency. In FIG. 2, orf179 corresponds to the region identified as the mutation frequency (mut) gene.

In addition the invention relates to a DNA sequence hybridizing to the DNA sequence having the sequence of nucleotides 1 to 579 (SEQ ID NO. 3) as shown in FIG. 4, said DNA sequence coding for a non-DNA polymerase protein having mutation-inducing activity.

The above DNA sequences may be used to develop probes capable of detecting and of isolating genes in organisms different from *Amycolatolsis methanolica*, said genes encoding a protein with an activity similar to that encoded by the sequence of nucleotides 1 to 579 (SEQ ID NO. 3) shown in FIG. 4.

Thus, the invention relates to the use of a nucleic acid probe comprising a nucleic acid sequence capable of hybridizing with the DNA sequence of nucleotides 1 to 579 (SEQ ID NO. 3) shown in FIG. 4 or the complementary strand thereof for the detection and/or isolation of a gene encoding a mutation-inducing non-DNA polymerase protein.

The development of probes and their use for detection and/or isolation of genes is well known to one of ordinary skill in the art.

Furthermore, the invention relates to an organism comprising DNA modified by the method according to the invention.

The invention also relates to a method of improving the genetical stability of an organism, wherein the organism comprises a gene encoding a mutation-inducing non-DNA polymerase protein and said gene is disabled by methods known per se.

It is well known that actinomycetes strains are often instable during large scale fermentations. Spontaneous occurring mutations result in reduced product yields at great cost. The method of stabilizing an organism according to the present invention allows for, for example, stabilizing organisms such as actinomycetes species and bacteria used for the production of, for example, metabolites such as amino acids and antibiotics.

Circumstantial evidence that the presence of mut genes are widespread in actinomycetes is that in natural, polluted environments they are among the first to evolve in the pollution degrading organisms.

Thus according to a preferred embodiment the method of improving the genetical stability of an organism is characterized in that the organism is an actinomycetes species, the actinomycetes species comprising a gene encoding a mutation-inducing non-DNA polymerase protein and said gene is disabled by methods known per se.

For organisms harboring pMEA300 or derivatives of pMEA300 the gene disabled by methods known per se comprises a functional nucleotide sequence chosen from pMEA300 or derivatives of pMEA300. To increase the viability of the organism it may be advantageous to disable the stf gene as well.

EXAMPLES

*Amycolatopsis methanolica* carrying the plasmid pMEA300 (wild type, wt) is available from the National Collection of Industrial Bacteria as NCIB11946 (Torry Research Station, Aberdeen, Scotland). *Amycolatopsis methanolica* strain WV1 is derived from NCIB11946 and differs from NCIB11946 in that the plasmid pMEA300 is not present. *Amycolatopsis methanolica* WV1 can be obtained by curing the plasmid from NCIB11946 using methods well known in the art. NCIB11946 was cured from pMEA300 by protoplast formation and regeneration (Moretti et al. 1985) and subsequently screening by Southern hybridization (Sambrook et al. 1989) for derivative strains of NCIB11946 that had lost pMEA300. The nucleic acid sequence of pMEA300 is available from the GenBank database accession no. L36679.

The mutation-inducing protein has a molecular weight of 21,721 and comprises 192 amino acids plus the "STP" codon (SEQ ID NO. 4). A restriction map of pMEA300 showing the location of the gene (mut) encoding this protein is shown in FIG. 2. The stimulating transformation frequency (stf) protein has a molecular weight of 40,233 and comprises 373 amino acids (SEQ ID NO. 2).

*A. methanolica* grows as chains of several cells, thus in the examples below the term colony forming unit is used (1 colony forming unit corresponding to about 10 cells).

Example I

Shikimate as a xenobiotic. *Amycolatopsis methanolica* (wild type; NCIB11946) and *Amycolatopsis methanolica* WV1 are not capable of growing on shikimate. The xenobiotic shikimate is neither available as a carbon source nor as an energy source (Euverink et al. 1992).

$1–5 \times 10^8$ colony forming units of *Amycolatopsis methanolica* NCIB11946 and WV1 respectively were incubated on agar plates (de Boer et al., 1988) and incubated at 37° C. in the presence of shikimate without any other carbon source present. After 10 days Shikimate-utilizing mutants of the wild type appeared at a frequency of $5.0 \times 10^{-7}$. Mutants of WV1 appeared at a 10 times lower frequency.

Example II

Overproduction of phenylalanine.

$1–5 \times 10^8$ colony forming units of *A. methanolica* NCIB11946 and WV1 respectively were grown on glucose minimal medium agar plates (de Boer et al. 1988) in the presence of 1 mg/ml para-fluorophenylalanine (pFPhe) at 37° C. pFPhe is a growth inhibiting analogue of phenylalanine. After prolonged incubation, pFPhe-resistant mutants of the wild-type gradually appeared, reaching a final frequency of $5.7 \times 10^{-4}$ after 6–8 days. Strain WV1 showed a markedly lower frequency ($2.0 \times 10^{-6}$), this latter frequency corresponding to the upper limit of the frequency of spontaneous mutation normally observed for other organisms.

Transformation of WV1 with pMEA300 resulted in a transformant exhibiting a similar frequency ($5.5 \times 10^{-4}$) as the wild-type.

Using the method described by Euverink et al. (1995), it was shown that the activity of the prephenate dehydratase and chorismate mutase enzymes was markedly increased. The enzymes were no longer sensitive for inhibition by phenylalanine. However, as wild-type *A. methanolica* possesses the enzymes to degrade any excess phenylalanine, the wild-type mutants obtained according to this example do not overproduce phenylalanine in the absence of pFPhe.

Example III

Plasmid pMEA300 Deletion Derivatives.

Deletion derivatives of pMEA300 were tested for the ability to restore in strain WV1 the high frequency of spontaneous resistance against pFPhe. Deletion derivatives pWV129, pWV136, pWV113 and pWV375 lack, respectively, the int and xis genes, the genes indicated by black arrows in FIG. 2 as a result of which conjugation is no longer possible, the stf and mut genes, and the stf gene. The table below shows the frequency of spontaneous resistance of the various strains. Orf179 was shown to be responsible for the increased mutation frequency.

| Strain | Frequency | Rel. Mutation Freq. | Plasmid Char. |
|---|---|---|---|
| wt | $5.9 \times 10^{-4}$ | 143 | wt |
| WV1 | $4.1 \times 10^{-6}$ | 1 | plasmid-free |
| WV1/pMEA300 | $5.6 \times 10^{-4}$ | 136 | wt |
| WV1/pWV129 | $13.0 \times 10^{-4}$ | 317 | no integration |
| WV1/pWV136 | $4.3 \times 10^{-4}$ | 104 | no conjugation |
| WV1/pWV113 | $1.3 \times 10^{-6}$ | 0.3 | no stf & orf179 |
| WV1/pWV375 | $6.0 \times 10^{-4}$ | 146 | no stf |

As can be seen, absence of integration of the gene in the chromosome results in higher mutation frequencies. It is thought that if there is no integration a higher number of plasmid copies is present and thus a higher level of expression of the mutation-inducing protein. Accordingly, a preferred embodiment of the present invention is characterized in that the vector comprises at least one gene for integrating the vector into the genome of the hostcell and that at least one of the genes for integrating into the genome is disabled. Thus for pMEA300 preferably at least one of the genes chosen from the group consisting of int, xis and att is disabled.

---

We claim:

1. A method of modifying DNA by subjecting the DNA to a mutation-inducing treatment, said method comprising the steps of bringing the DNA to be mutated and a DNA sequence encoding a mutation-inducing non-DNA polymerase protein together in cells, said DNA sequence consisting of the sequence of nucleotides 34 to 612 of SEQ ID NO. 3, also shown as the "mut" gene in FIG. 4, or sequences encoding functional fragments thereof, growing the cells in the presence of a stress factor, and selecting the mutant cells which have developed a desirable trait in the presence of said stress factor.

2. The method of claim 1 wherein the desirable trait is selected from the overproduction of amino acids, antibiotics or proteins and the degradation of xenobiotics.

3. The method of claim 1, further comprising separating the DNA to be mutated and the DNA sequence encoding a mutation-inducing protein after the induction of mutations.

4. The method of claim 3, wherein the DNA sequence encoding a mutation-inducing protein resides in a vector, and further comprising transforming the cells containing the DNA to be mutated with said vector, selecting desirable mutant cells and curing said vector from the desirable cells.

5. The method of claim 4, wherein the vector is pMEA300.

6. The method of claim 3, wherein the DNA to be mutated resides in a vector, and further comprising transforming the cells carrying the DNA sequence encoding a mutation-inducing protein with said vector, selecting a desirable mutant organism and using the mutated vector to transform a second organism.

7. The method of claim 6, wherein the vector comprises at least one gene for integrating the vector into the genome of the host cell and that at least one of the genes for integrating into the genome is disabled.

8. The method of claim 1, wherein the stress factor is selected from xenobiotics, carbon sources which are not suitable substrates for the organism, and compounds limiting the production of products produced by the organism.

9. A prokaryote or lower eukaryote comprising DNA modified according to claim 1.

10. A prokaryote or lower eukaryote comprising a DNA sequence which encodes a mutation-inducing, non-DNA polymerase protein said DNA sequence consisting of the sequence of nucleotides 34 to 612 of SEQ ID NO. 3, also shown as the "mut" gene in FIG. 4.

11. An isolated DNA sequence encoding a mutation-inducing non-DNA polymerase protein, said isolated DNA sequence consisting of the sequence of nucleotides 34 to 612 of SEQ ID NO. 3, also shown as the "mut" gene in FIG. 4.

12. A method of improving the genetic stability of an organism, wherein the organism comprises a gene comprising a DNA sequence encoding a mutation-inducing non-DNA polymerase protein, said DNA sequence consisting of the sequence of nucleotides 34 to 612 of SEQ ID NO. 3, also shown as the "mut" gene in FIG. 4, and said gene is disabled.

13. The method of claim 12, wherein the organism is an actinomycetes species.

14. The method of claim 12, wherein the stf gene is disabled.

* * * * *